United States Patent
Wu et al.

(10) Patent No.: US 8,558,540 B2
(45) Date of Patent: Oct. 15, 2013

(54) METHOD OF MEASURING DIMENSIONLESS COUPLING CONSTANT OF MAGNETIC STRUCTURE

(75) Inventors: Te-Ho Wu, Yunlin County (TW); Lin-Hsiu Ye, Yunlin County (TW); Ying-Chuen Luo, Yunlin County (TW)

(73) Assignee: National Yunlin University of Science and Technology, Yunlin County (TW)

( * ) Notice: Subject to any disclaimer, the term of this patent is extended or adjusted under 35 U.S.C. 154(b) by 260 days.

(21) Appl. No.: 13/253,986

(22) Filed: Oct. 6, 2011

(65) Prior Publication Data
US 2013/0009633 A1 Jan. 10, 2013

(30) Foreign Application Priority Data
Jul. 4, 2011 (TW) .............................. 100123535 A

(51) Int. Cl.
*G01N 27/72* (2006.01)
*G11C 11/16* (2006.01)
*G01R 33/14* (2006.01)

(52) U.S. Cl.
USPC ............ 324/224; 365/158; 365/171; 324/223

(58) Field of Classification Search
USPC ................................................ 324/223, 224
See application file for complete search history.

(56) References Cited

U.S. PATENT DOCUMENTS

| 6,744,086 | B2 * | 6/2004 | Daughton et al. | 257/295 |
| 2007/0115718 | A1 * | 5/2007 | Sharma et al. | 365/171 |
| 2009/0068500 | A1 * | 3/2009 | Kong et al. | 428/846.6 |
| 2009/0081484 | A1 * | 3/2009 | Watanabe | 428/828 |
| 2010/0266873 | A1 * | 10/2010 | Wu et al. | 428/826 |

* cited by examiner

*Primary Examiner* — Patrick Assouad
*Assistant Examiner* — Hoang X Nguyen
(74) *Attorney, Agent, or Firm* — CKC & Partners Co., Ltd.

(57) ABSTRACT

In A method for measuring a dimensionless coupling constant of a magnetic structure includes the following steps. A step of applying an external vertical magnetic field is performed for enabling magnetic moments of a RE-TM (Rare Earth-Transition metal) alloy magnetic layer of the magnetic structure to be vertical and saturated. A step of measuring a compensation temperature is performed when the sum of the magnetization of the RE-TM alloy magnetic layer is zero. A step of applying an external parallel magnetic field to the RE-TM alloy magnetic layer is performed. A step of adjusting the temperature of the magnetic structure to the compensation temperature and measuring a hysteresis loop of the magnetic structure under the external parallel magnetic field is performed, wherein the inverse of the slope of hysteresis loop is a dimensionless coupling constant.

2 Claims, 13 Drawing Sheets

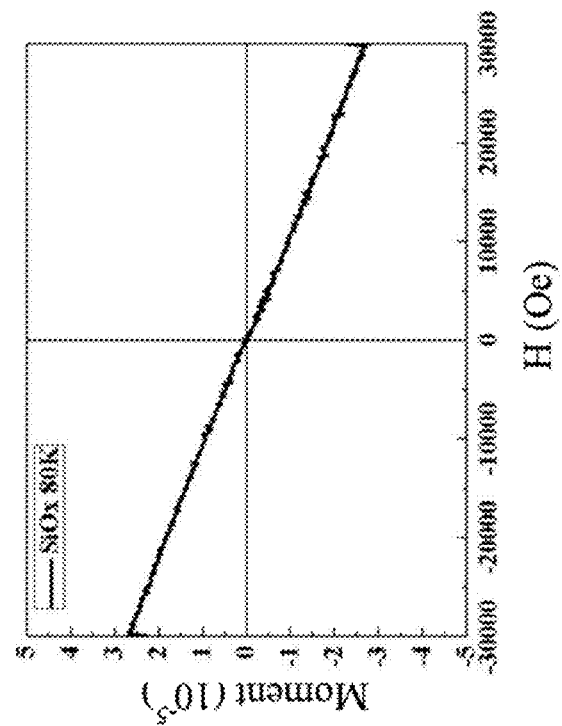
multiplying the area of the magnetic structure
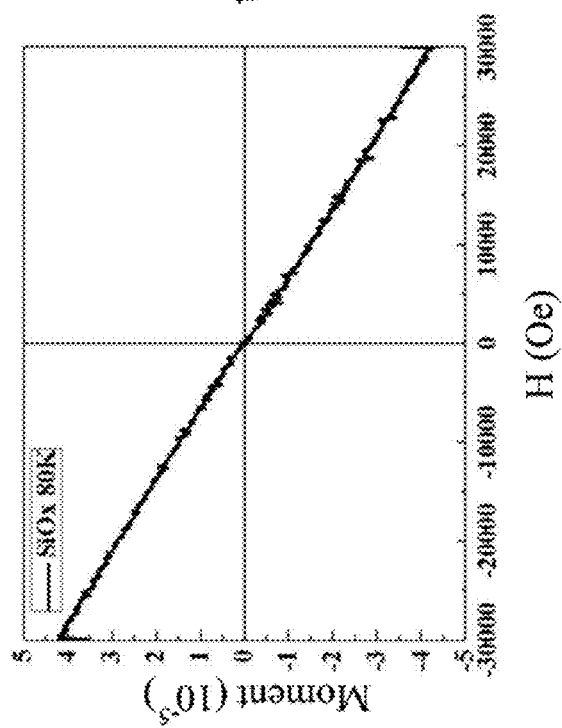
Fig. 5C-1

METHOD OF MEASURING DIMENSIONLESS COUPLING CONSTANT OF MAGNETIC STRUCTURE

RELATED APPLICATIONS

The application claims priority to Taiwan Application Serial Number 100123535, filed Jul. 4, 2011, which is herein incorporated by reference.

BACKGROUND

1. Technical Field

The present invention relates to a method of measuring a dimensionless coupling constant of a magnetic structure.

2. Description of Related Art

Magnetization M of a RE-TM (Rare Earth-Transition metal) magnetic structure is composed of two subnetwork magnetizations which are RE magnetization $M_R$ and TM magnetization $M_T$. When a RE-dominant case is discussed, a total energy is described In terms of $M_R$ and $M_T$, and the subnetwork anisotropy constants $K_R$ and $K_T$ as follows:

$$E_{tot} = H[M_R \cos(\alpha-\theta_R) - M_T \cos(\alpha-\theta_T)] + [K_R \sin^3 \theta_R + K_T \sin^2 \theta_T] + 2\pi (M_R \cos\theta_R - M_T \cos\theta_T)^2 - \lambda M_R M_T \cos(\theta_R - \theta_T),$$

wherein $H[M_R \cos(\alpha-\theta_R) - M_T \cos(\alpha-\theta_T)]$ is an external energy density; $[K_R \sin^3 \theta_R + K_T \sin^2 \theta_T]$ is an anisotropy energy density; $2\pi(M_R \cos\theta_R - M_T \cos\theta_T)^2$ is a demagnetizing energy density; and $\lambda M_R M_T \cos(\theta_R - \theta_T)$ is an exchange coupling energy density between RE and TM subnetworks. By calculating the exchange energy between RE and TM atoms per unit volume, the dimensionless coupling constant $\lambda$ is defined as $$\lambda = \frac{2(Z+1)|J_{RE-TM}|}{NG_{RE}g_{TM}\mu_B^2},$$

wherein Z is an average coordination number (number of nearest neighbor atoms); $2J_{RE-TM}$ is the exchange energy per RE-TM pair; N is the total atomic number density; $g_{RE}$ and $g_{TM}$ are gyromagnetic factors; and $\mu_B$ ($=9.27 \times 10^{-21}$ emu) is the Bohr magneton. Therefore, the magnetization reversal intensity can be estimated by the dimensionless coupling constant $\lambda$.

Referring to FIG. 1A and FIG. 1B. FIG. 1A is a schematic diagram showing the relationships between the saturation magnetization $M_S$ of the magnetic structure and the composition of the magnetic structure, and between the coercivity Hc of the magnetic structure and the composition of the magnetic structure. FIG. 1B is a schematic diagram showing the relationships between the net magnetization $M_{NET}$ of the magnetic structure and the temperature of the magnetic structure, and between the coercivity Hc of the magnetic structure and the temperature of the magnetic structure. In FIG. 1A, the x-axes represents the percentage of the RE atomic content, and the y-axes represents the saturation magnetization $M_S$ of the magnetic structure, wherein TM rich represents that the RE atomic content is less than the compensation point content (the compensation point content represents the percentage of the RE atomic content when RE magnetization $M_R$ and TM magnetization $M_T$ are equal in size and opposite in direction), and RE rich represents that the RE atomic content is more than the compensation point content. The saturation magnetization $M_S$ is zero when the compensation point content is reached, the coercivity Hc is maximum; and the dimensionless coupling constant $\lambda$ is proportional to the coercivity Hc. Therefore, when the RE atomic content is closer to the compensation point content, the greater external magnetic field is needed to reverse the magnetic moments. In FIG. 1B, when the net magnetization $M_{NET}$ is zero, the temperature is a compensation point temperature.

FIG. 2 is a schematic diagram showing the size and direction of to magnetization of the magnetic structure in a RE-dominant case. In FIG. 2, RE magnetization $M_R$ and TM magnetization $M_T$ are represented by two dimensional (2D) vectors, and M is the sum of the vectors. When the temperature of the magnetic structure is near the compensation point, the magnetizations $M_R$ and $M_T$ are anti-parallel to make M zero.

$\theta_R$ and $\theta_T$ are very small when the temperature of the magnetic structure is near to the compensation point, so that the $E_{tot}$ equation can be solved by neglecting terms $\theta^2_R$ and $\theta^2_T$. Moreover, the subnetwork anisotropy fields are defined herein as $H_R = 2K_R/M_R$ and $H_T = 2K_T/M_T$, and the solutions of the $E_{tot}$ equation in case of $M_R > M_T$ can be written as follows:

$$\theta_R = \frac{H\sin\alpha(\lambda M_s + H_T - H\cos\alpha)}{\lambda(2K_R + 2K_T - 4\pi M_s^2 + HM_s\cos\alpha) + (H_T - H\cos\alpha + 4\pi M_s)(H_R + H\cos\alpha - 4\pi M_s)}$$

$$\theta_T = \frac{H\sin\alpha(\lambda M_s - H_R - H\cos\alpha)}{\lambda(2K_R + 2K_T - 4\pi M_s^2 + HM_s\cos\alpha) + (H_T - H\cos\alpha + 4\pi M_s)(H_R + H\cos\alpha - 4\pi M_s)}$$

The above solutions includes four unknowns: $\lambda$, $M_R$ or $M_T$ ($M_S = |M_R - M_T|$ can be measured by Alternating Gradient Magnetometer (AGM)), $K_R$ and $K_T$. Therefore, it is a complicated problem to find $\lambda$ experimentally.

SUMMARY

According to one embodiment of the present disclosure, a dimensionless coupling constant of a magnetic structure is disclosed, wherein the magnetic structure includes, from a bottom layer to a top layer, a substrate, a first metal layer, a RE-TM (Rare Earth-Transition) alloy magnetic layer, a buffer layer and a second metal layer. In the method, a step of applying an external vertical magnetic field is performed, wherein a temperature of the magnetic structure is reduced to 50K, and the external vertical magnetic field is applied to the RE-TM alloy magnetic layer of the magnetic structure, thereby enabling magnetic moments of the RE-TM alloy magnetic layer to be vertical and saturated. A step of measuring a compensation temperature is performed, wherein the external vertical magnetic field is removed, and the compensation temperature is measured when the sum of the magnetization of the RE-TM alloy magnetic layer is zero. A step of applying an external parallel magnetic field to the RE-TM alloy magnetic layer is performed. A step of adjusting the temperature of the magnetic structure to the compensation temperature and measuring a hysteresis loop of the magnetic structure under the external parallel magnetic field is performed, wherein the inverse of the slope of hysteresis loop is a dimensionless coupling constant.

BRIEF DESCRIPTION OF THE DRAWINGS

FIG. 5B-1 to FIG. 5B-4 show respective hysteresis loops of the magnetic structures of the first fourth embodiments at the compensation point $T_{comp}$ under an external parallel magnetic field;

FIG. 5C-1 to FIG. 5C-4 show respective hysteresis loops of the substrates of the first to fourth embodiments at the compensation point $T_{comp}$ under an external parallel magnetic field, and the hysteresis loops after the hysteresis loops are multiplied by the areas of the magnetic structures respectively; and FIG. 5D-1 to FIG. 5D-4 show the hysteresis loops which are obtained by subtracting the hysteresis loops of FIG. 5C-1 to FIG. 5C-4 from hysteresis loops of FIG. 5B-1 to FIG. 5B-4 and multiplying by the areas of the magnetic structures respectively.

DETAILED DESCRIPTION

Since RE magnetization $M_R$ and TM magnetization $M_T$ has the same quantity and opposite directions (anti-parallel) when the magnetic structure is kept at the compensation point $T_{comp}$, the sum of the magnetization $M_S$ is zero. Meanwhile, when an external parallel magnetic field is applied to the magnetic structure, the slant angles of RE magnetization $M_R$ and TM magnetization $M_T$ will be different. Therefore, a parallel magnetization $M_{//}$ parallel to the magnetic structure can be obtained, thereby simplifying the solution of $E_{tot}$ equation. Further, when $M_R = M_T$ ($M_S = 0$) and $\alpha = 90°$, the total parallel magnetization $M_{//}$ can be written as $$M_{//} = M_R \sin\theta_R - M_T \sin\theta_T = \frac{H}{\lambda};$$

accordingly, $$\lambda \cong \frac{H}{M_{//}}$$

is obrained.

Figure 1B:
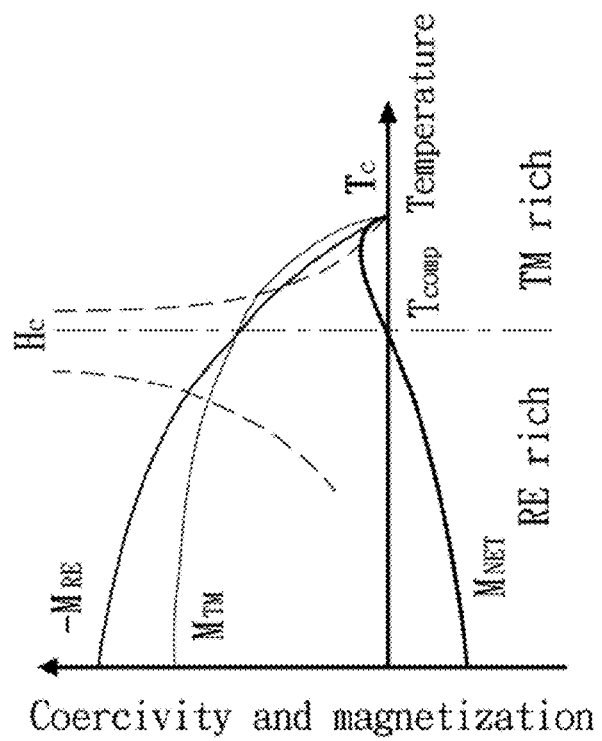
FIG. 1B is a schematic diagram showing the relations between the net magnetization $M_{NET}$ of the magnetic structure and the temperature, and between the coercivity Hc of the magnetic structure and the temperature.
Figure 1A:
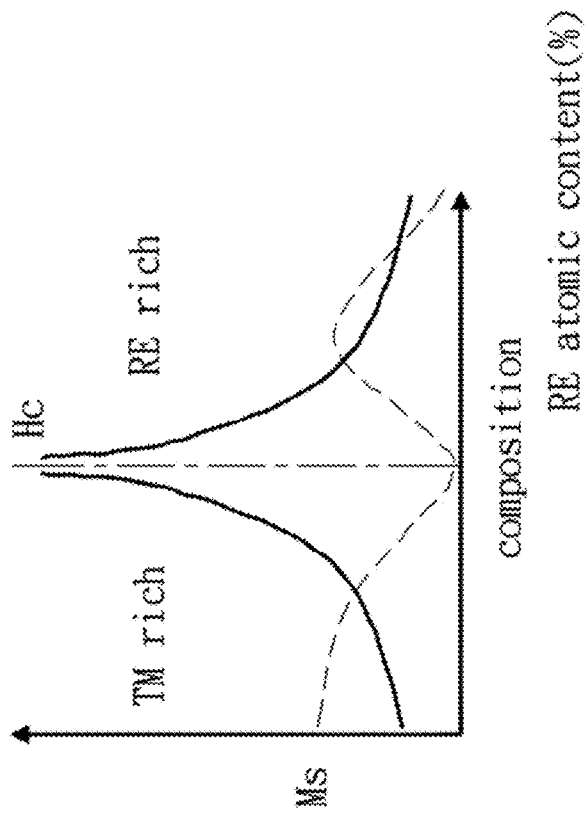
FIG. 1A is a schematic diagram showing the relations between the saturation magnetization $M_S$ of the magnetic structure and the composition, and between the coercivity Hc of the magnetic structure and the composition.
Figure 2:
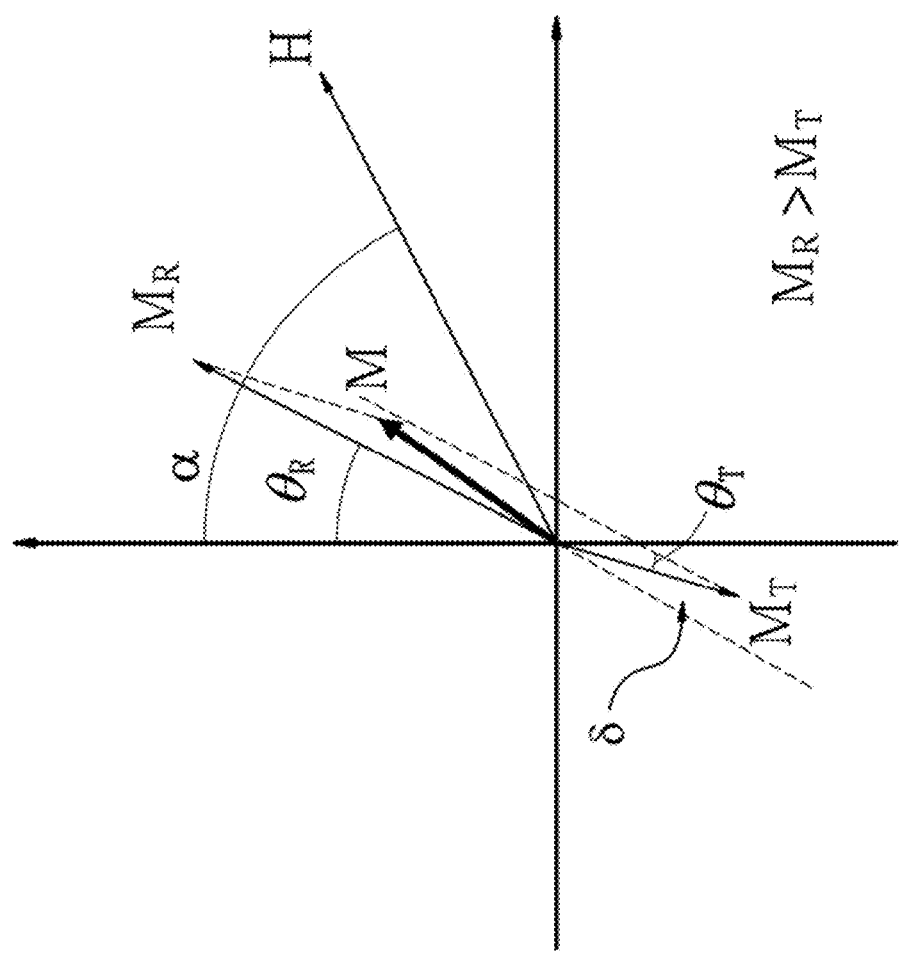
FIG. 2 is a schematic diagram showing that the magnetization and the direction thereof based on the RE-dominant.
Figure 3:
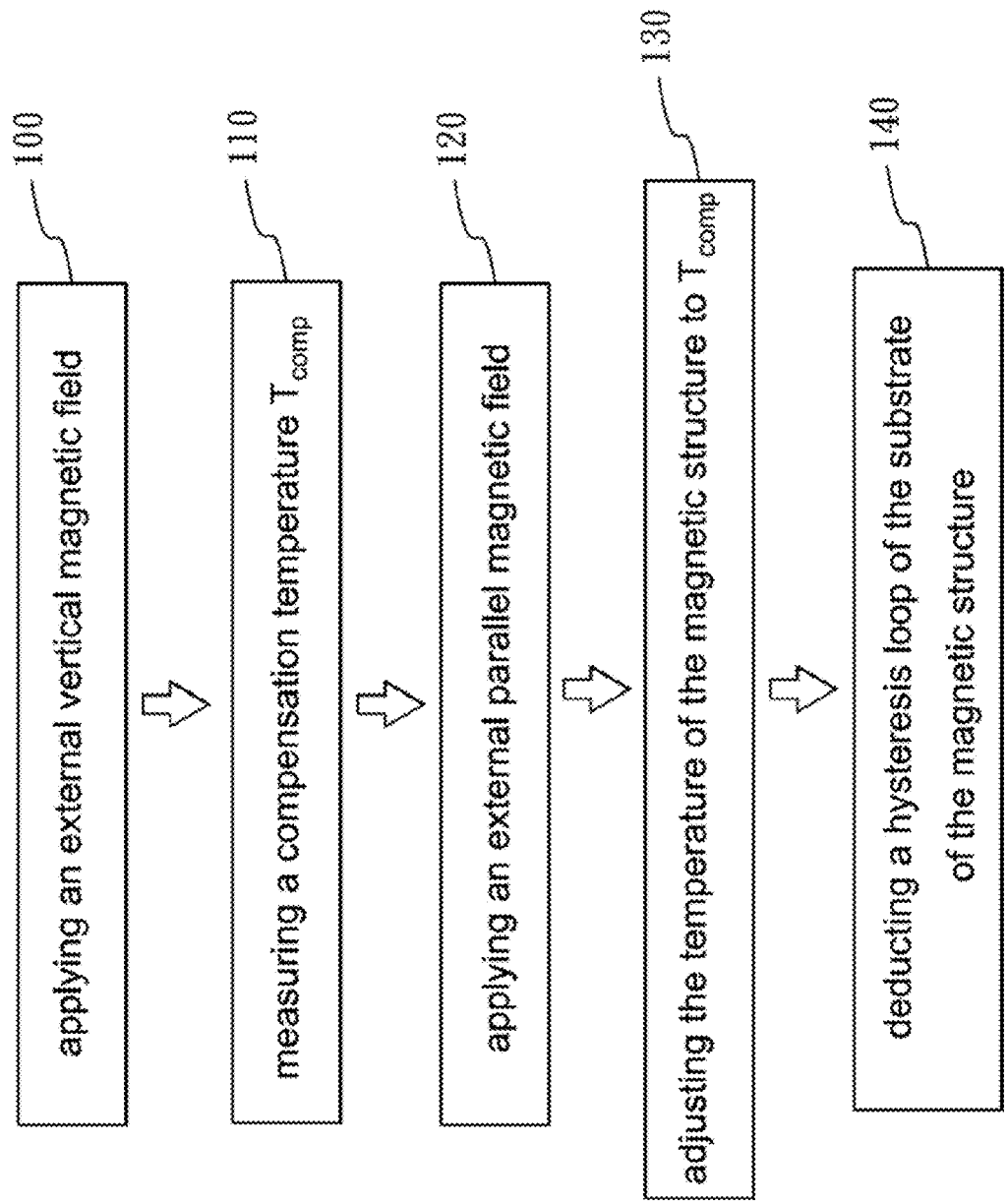
FIG. 3 is a flow chart showing a method for measuring a dimensionless coupling constant of a magnetic structure according to one embodiment of the present disclosure.
Figure 4:
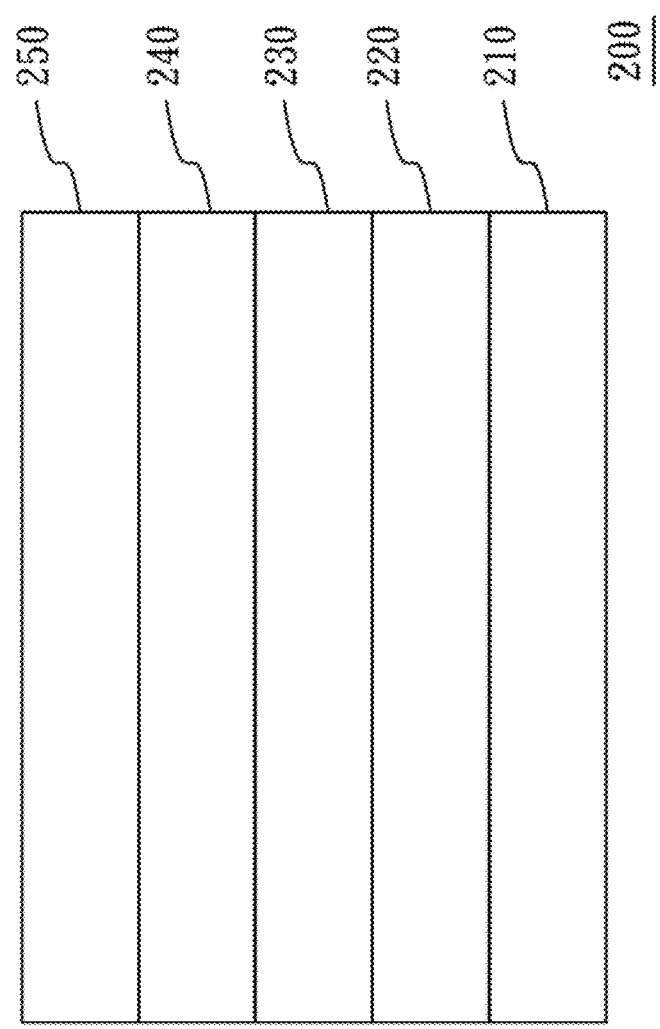
FIG. 4 is a schematic view of a magnetic structure desired to be measured by the method of FIG. 3.

Referring to FIG. 3 and FIG. 4. FIG. 3 is a flow chart showing the method for measuring a dimensionless coupling constant of a magnetic structure according to one embodiment of the present disclosure; and FIG. 4 is a schematic view of a magnetic structure desired to be measured by the method of FIG. 3. The magnetic structure 200 includes a substrate 210, a first metal layer 220, a RE-TM alloy magnetic layer 230, a buffer layer 240 and a second metal layer 250, wherein the first metal layer 220, the RE-TM alloy magnetic layer 230, the buffer layer 240 and the second metal layer 250 are stacked up on the substrate 210 in sequence.

Step 100 is a step of applying an external vertical magnetic field, wherein a temperature of the magnetic structure 200 is reduced to 50K, and an external vertical magnetic field is applied to the RE-TM alloy magnetic layer 230 of the magnetic structure, thereby enabling magnetic moments of the RE-TM alloy magnetic layer 230 to be vertical and saturated.

Step 110 is a step of measuring a compensation temperature, wherein the external vertical magnetic field is removed, and the compensation temperature $T_{comp}$ of the is measured when the sum of the magnetization of the RE-TM alloy magnetic layer 230 is zero, wherein, at the compensation temperature $T_{comp}$, RE magnetization $M_R$ and TM magnetization $M_T$ has the same quantity and opposite directions (anti-parallel), M is zero Step 120 is a step of applying an external parallel magnetic field, wherein an external parallel magnetic field is applied to the RE-TM alloy magnetic layer 230, and the compensation temperature $T_{comp}$ at which RE magnetization $M_R$ and TM magnetization $M_T$ are zero is measured, wherein the compensation temperature $T_{comp}$ is the temperature point when the magnetization is zero in the magnetic moment-temperature chart. Accordingly, in order to ensure the consistency of the experiment, the temperature of the magnetic structure 200 is also reduced to 50K, and then is increased to the compensation temperature $T_{comp}$ during applying the external parallel magnetic field.

Step 130 is a step of adjusting the temperature of the magnetic structure to the compensation temperature $T_{comp}$, wherein the temperature of the magnetic structure 200 is adjusted to the compensation temperature $T_{comp}$, and a hysteresis loop of the magnetic structure 200 is measured under the external parallel magnetic field.

Step 140 is a step of subtracting a hysteresis loop of the substrate of the magnetic structure. When the magnetization and magnetic moment change of the RE-TM alloy magnetic layer 230 is measured, since to the background signals of the substrate 210 are too strong, the accuracy of the measured result is easily to be affected. Therefore, after measuring the hysteresis loop of the magnetic structure 200, the hysteresis loop of the substrate 210 under the external parallel magnetic field should be subtracted therefrom, and an inverse of a slope of the hysteresis loop thereof is a dimensionless coupling constant.

Figure 5A:
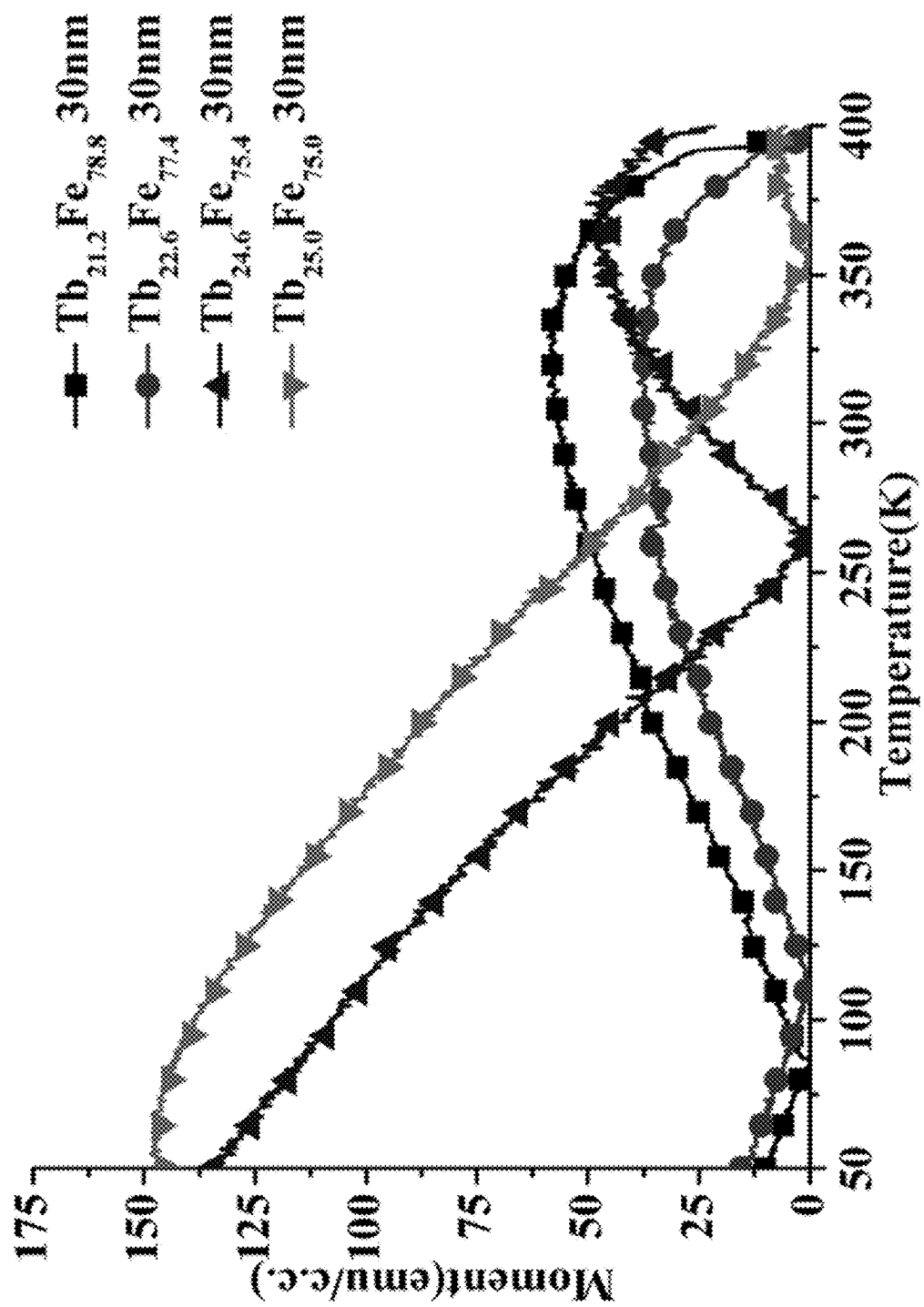
FIG. 5A is a Temperature-Moment diagram of the magnetic structures with different compositions according to the first to fourth embodiments of the present disclosure.

FIG. 5A is a Temperature-Moment diagram of the magnetic structures with different compositions according to the first embodiment to the fourth embodiments of the present disclosure, wherein the magnetic structures of the first embodiment to fourth embodiments are different percentage of composition. In FIG. 5A, the magnetic structure 200 includes the $SiO_x$ substrate 210, the Ta (5 nm in thickness) first metal layer 220, the TbFe (5 nm or more in thickness) RE-TM alloy magnetic layer 230, a MgO (1 nm in thickness) buffer layer 240 and a Ta (5 nm in thickness) second metal layer 250. The RE-TM alloy magnetic layer 230 also can be GdFe, DyFe, TbFeCo, GdFeCo and DyFeCo, etc., and will not be stated herein again.

Figures 2, 5B:
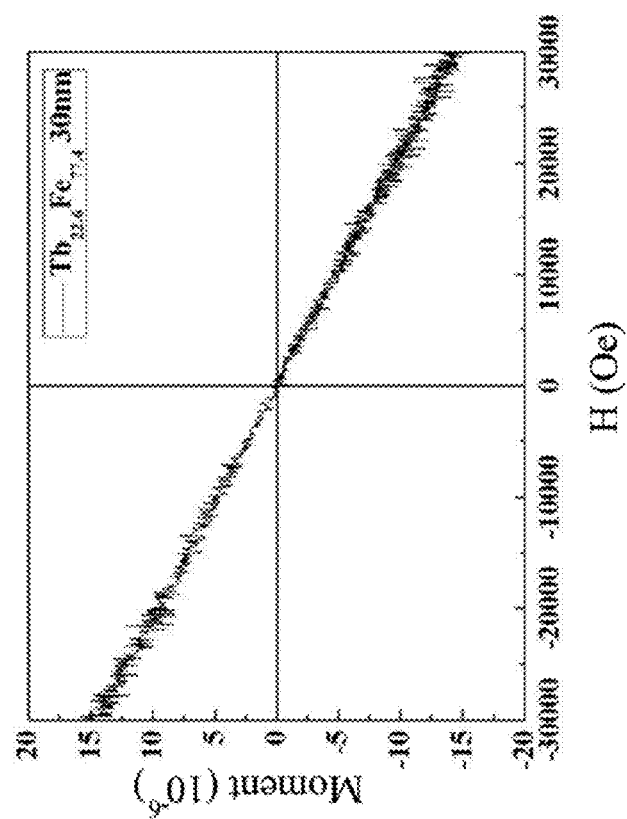
Figures 1, 5B:
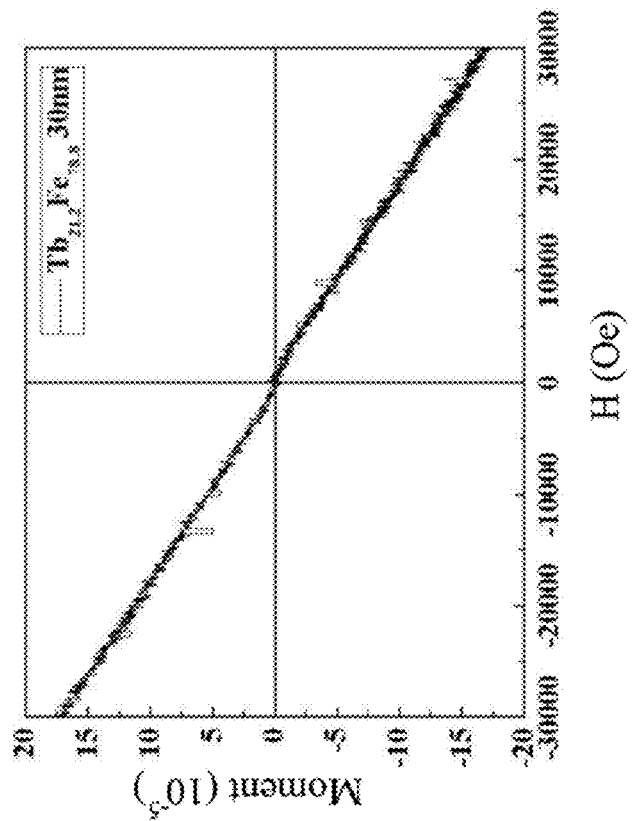
Figures 4, 5B:
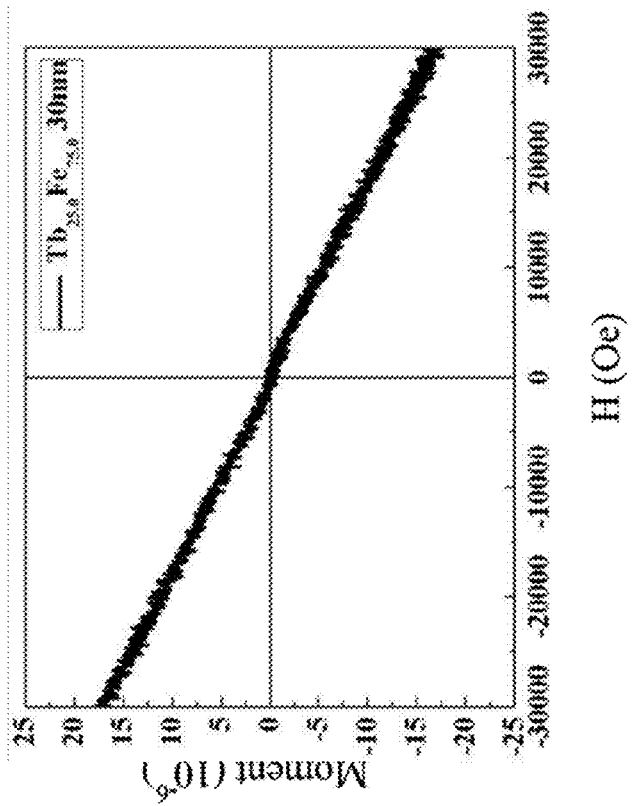
Figures 3, 5B:
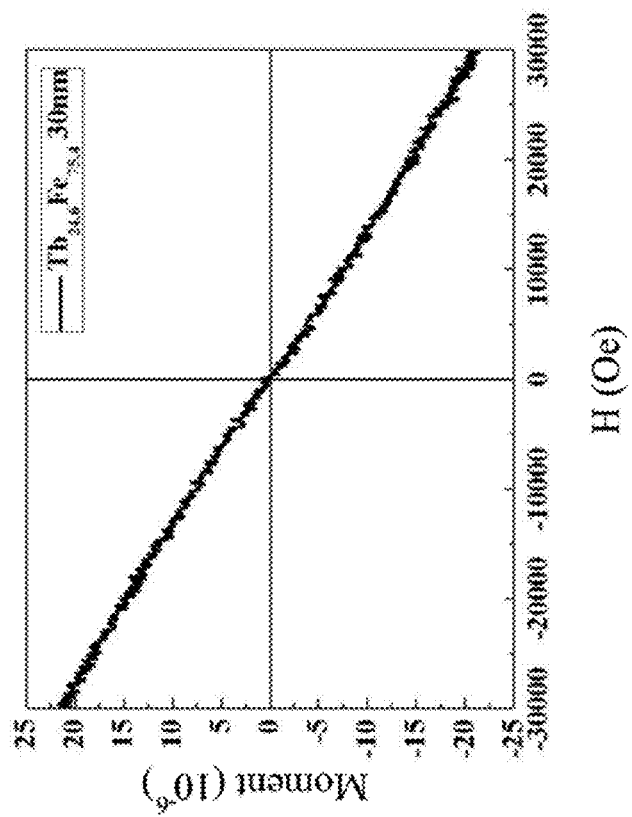
Figures 2, 5C:
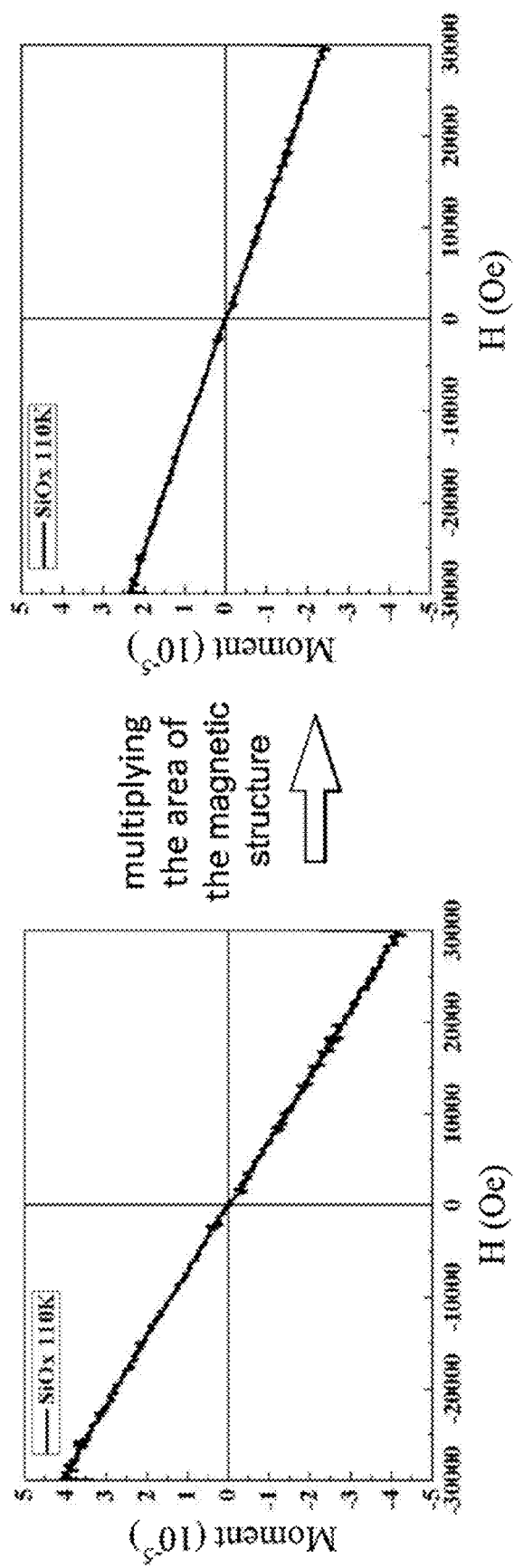
Figures 3, 5C:
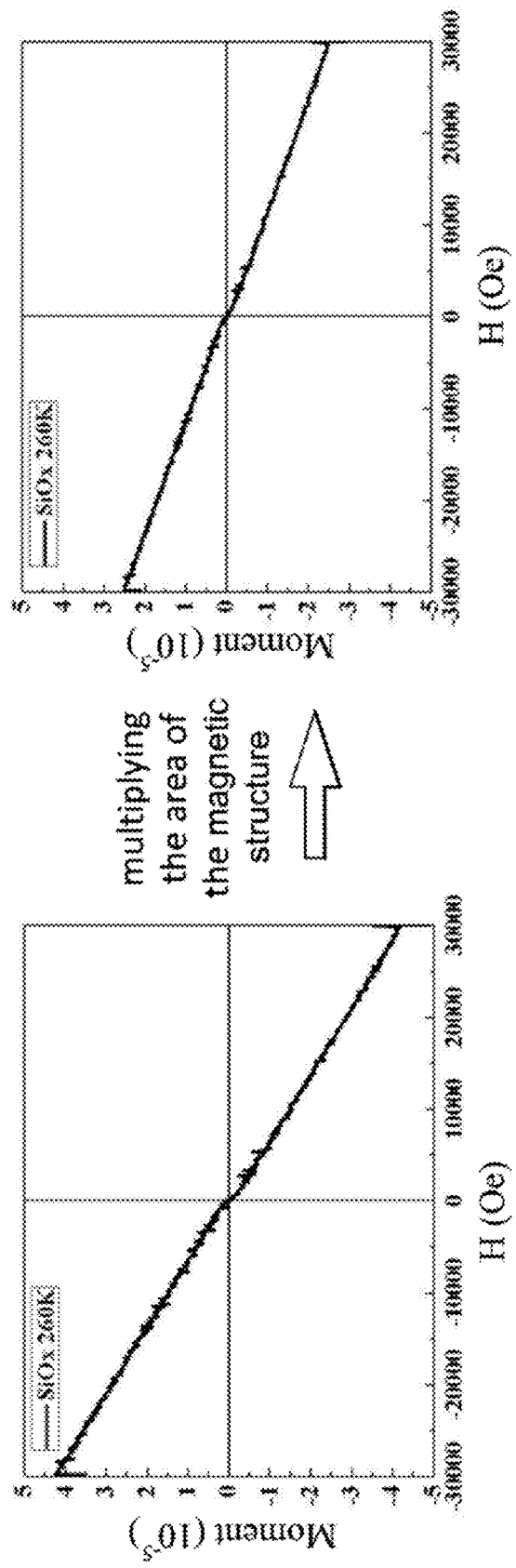
Figure 5C:
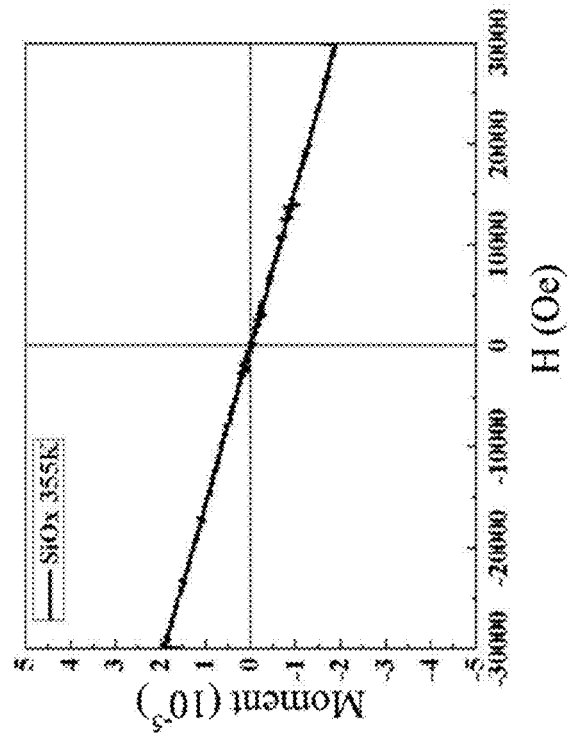
Figure 4:
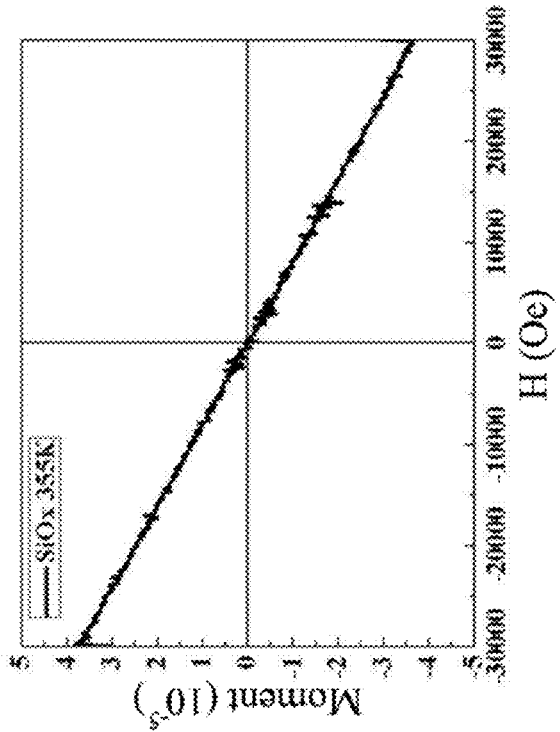
Figures 2, 5D:
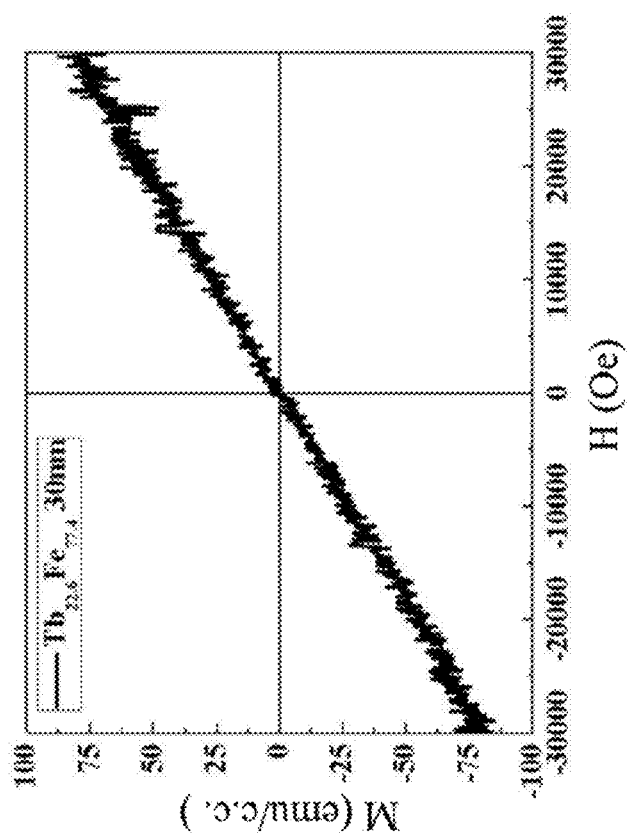
Figures 1, 5D:
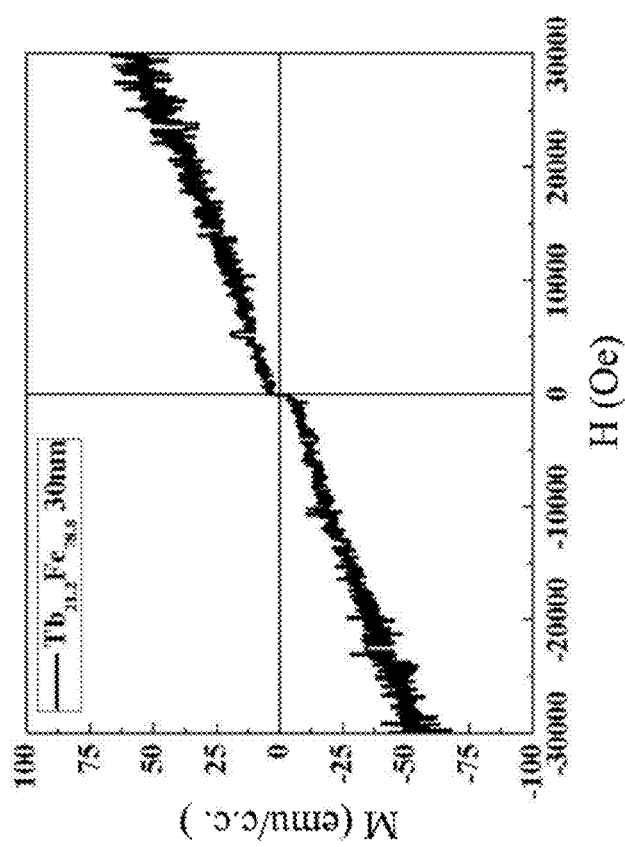
Figures 4, 5D:
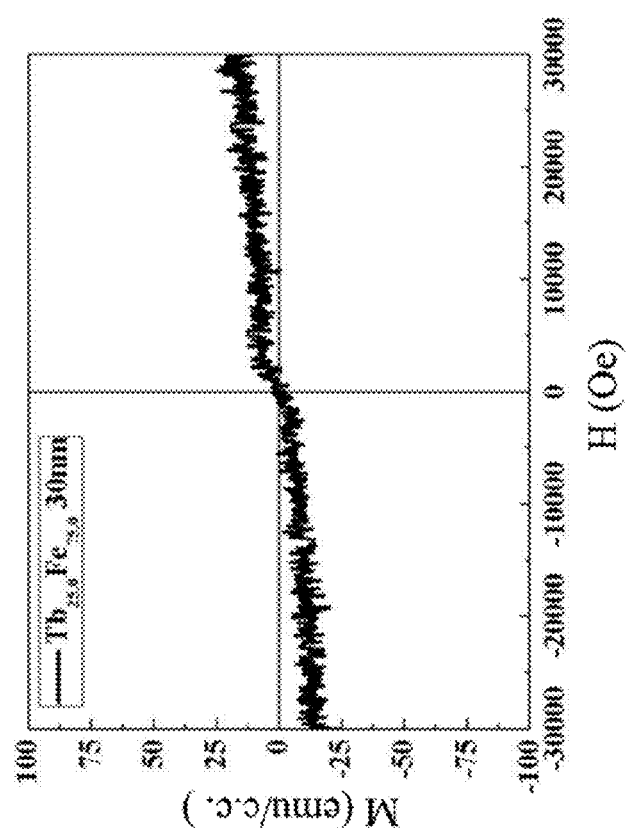
Figures 3, 5D:
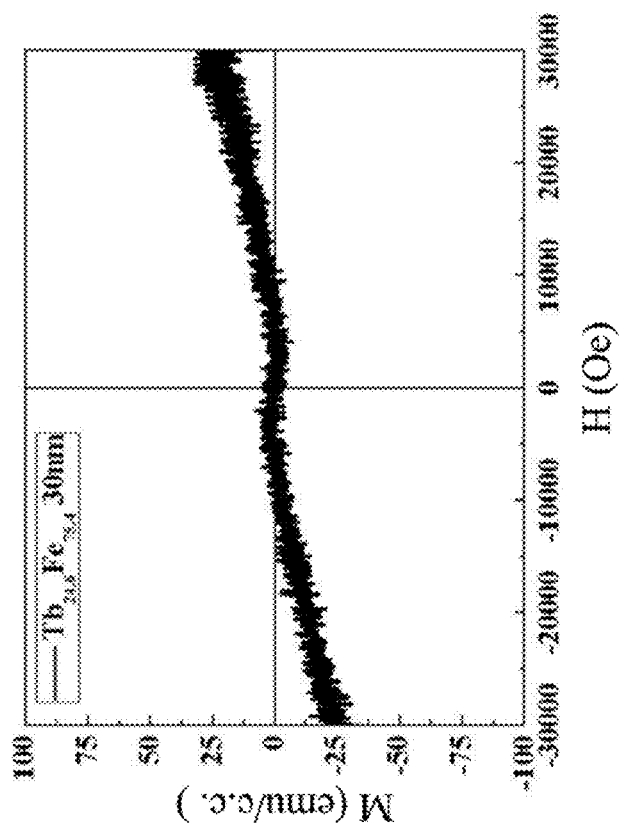

FIG. 5B-1 to FIG. 5B-4 show respective hysteresis loops of the magnetic structures 200 of the first to the fourth embodiments at the compensation point $T_{comp}$ under an external parallel magnetic field. FIG. 5C-1 to FIG. 5C-4 show respective hysteresis loops of the substrates 210 of the first to the fourth embodiments at the compensation point $T_{comp}$ under an external parallel magnetic field, and the hysteresis loops after the hysteresis loops are multiplied by the area of the magnetic structures 200 respectively. FIG. 5D-1 to FIG. 5D-4 show the hysteresis loops which are obtained by subtracting the hysteresis loops of FIG. 5C-1 to FIG. 5C-4 from hysteresis loops of FIG. 5B-1 to FIG. 5B-4, and multiplying by the areas of the magnetic structures 200 respectively, and the inverses of the slopes of the hysteresis loops in FIG. 5D-1 to FIG. 5D-4 are dimensionless coupling constants $\lambda$. $\lambda$ of the first embodiment is 460; $\lambda$ of the second embodiment is 418; $\lambda$ of the third embodiment is 916; and $\lambda$ of the fourth embodiment is 1992.

It will be apparent to those skilled in the art that various modifications and variations can be made to the structure of the present invention without departing from the scope or spirit of the invention. In view of the foregoing, it is intended that the present invention cover modifications and variations of this is invention provided they fall within the scope of the following claims.

What is claimed is:

1. A method for measuring a dimensionless coupling constant of a magnetic structure, wherein the magnetic structure comprises, from a bottom layer to a top layer, a substrate, a first metal layer, a RE-TM (Rare Earth-Transition) alloy magnetic layer, a buffer layer and a second metal layer, the method comprising:

performing a step of applying an external vertical magnetic field, wherein a temperature of the magnetic structure is reduced to 50K, and the external vertical magnetic field is applied to the RE-TM alloy magnetic layer of the magnetic structure, thereby enabling magnetic moments of the RE-TM alloy magnetic layer to be vertical and saturated;

performing a step of measuring a compensation temperature, wherein the external vertical magnetic field is removed, and the compensation temperature is measured when the sum of the magnetization of the RE-TM alloy magnetic layer is zero;

performing a step of applying an external parallel magnetic field to the RE-TM alloy magnetic layer; and performing a step of adjusting the temperature of the magnetic structure to the compensation temperature and measuring a hysteresis loop of the magnetic structure under the external parallel magnetic field, wherein an inverse of a slope of the hysteresis loop is a dimensionless coupling constant.

2. The method of claim 1, further comprising:

performing a step of subtracting a hysteresis loop of the substrate of the magnetic structure, wherein after the step of adjusting the temperature of the magnetic structure to the compensation temperature, the hysteresis loop of the substrate under the external parallel magnetic field is measured, and then the hysteresis loop of the substrate is subtracted from the hysteresis loop of the magnetic structure, thereby obtaining the inverse of the slope of the hysteresis loop after subtraction, which is the dimensionless coupling constant.

* * * * *